(12) United States Patent
Mietzner et al.

(10) Patent No.: US 10,370,629 B2
(45) Date of Patent: Aug. 6, 2019

(54) VARIABLE DIAMETER BIOREACTORS

(71) Applicant: Lonza Limited, Visp (CH)

(72) Inventors: Michael Mietzner, Fremont, NH (US); Rajesh Beri, Westford, MA (US); Edward Gunderson, Nottingham, NH (US)

(73) Assignee: Lonza Limited, Visp (CH)

( * ) Notice: Subject to any disclaimer, the term of this patent is extended or adjusted under 35 U.S.C. 154(b) by 7 days.

(21) Appl. No.: 15/629,886

(22) Filed: Jun. 22, 2017

(65) Prior Publication Data

US 2017/0369828 A1 Dec. 28, 2017

Related U.S. Application Data

(60) Provisional application No. 62/354,216, filed on Jun. 24, 2016.

(51) Int. Cl.
*C12M 1/00* (2006.01)
*C12M 1/06* (2006.01)
*C12P 21/00* (2006.01)
*C12M 1/36* (2006.01)

(52) U.S. Cl.
CPC ............ *C12M 23/02* (2013.01); *C12M 23/14* (2013.01); *C12M 23/28* (2013.01); *C12M 27/02* (2013.01); *C12M 41/48* (2013.01); *C12M 43/00* (2013.01); *C12P 21/00* (2013.01); *C12P 21/005* (2013.01)

(58) Field of Classification Search
CPC ...................................................... C12M 23/02
See application file for complete search history.

(56) References Cited

U.S. PATENT DOCUMENTS

| | | |
|---|---|---|
| 4,762,684 A | 8/1988 | Chantriaux et al. |
| 5,081,036 A | 1/1992 | Familletti |
| 5,656,491 A | 8/1997 | Cassani et al. |
| 6,168,944 B1 | 1/2001 | Condon et al. |
| 7,629,167 B2 | 12/2009 | Hodge et al. |
| 8,298,054 B2 | 10/2012 | Hodge et al. |
| 8,771,635 B2 | 7/2014 | Mohtadi et al. |
| 9,388,373 B2 | 7/2016 | Rao et al. |
| 9,670,446 B2 | 6/2017 | Khan |
| 2003/0113915 A1 | 6/2003 | Heidemann et al. |
| 2008/0199950 A1 | 8/2008 | Luk et al. |
| 2009/0305626 A1 | 12/2009 | Hope |
| 2010/0028990 A1 | 2/2010 | Broadley et al. |
| 2011/0151506 A1 | 6/2011 | Calvosa et al. |

(Continued)

FOREIGN PATENT DOCUMENTS

WO WO 2017/072201 A2 5/2017

OTHER PUBLICATIONS

International Search Report (PCT/ISA/220 & PCT/ISA/210) issued in PCT Application No. PCT/US2017/038670 dated Sep. 15, 2017 (Three (3) pages).

(Continued)

*Primary Examiner* — Rosanne Kosson
(74) *Attorney, Agent, or Firm* — Crowell & Moring LLP

(57) ABSTRACT

A variable diameter bioreactor vessel is provided that includes a first vessel section having a first diameter configured to hold a liquid media and biologic material, and a second vessel section having a second diameter that is greater than the first diameter such that the liquid media can be increased from a first volume to a second volume within the vessel.

15 Claims, 10 Drawing Sheets

(56) References Cited

U.S. PATENT DOCUMENTS

| | | | |
|---|---|---|---|
| 2011/0312087 A1* | 12/2011 | Khan | C12M 27/02 435/325 |
| 2012/0077429 A1 | 3/2012 | Wernimont et al. | |
| 2014/0030762 A1 | 1/2014 | Deplano et al. | |
| 2014/0135540 A1 | 5/2014 | Iversen | |
| 2016/0097074 A1 | 4/2016 | Collins et al. | |

OTHER PUBLICATIONS

Written Opinion (PCT/ISA/237) issued in PCT Application No. PCT/US2017/038670 dated Sep. 15, 2017 (Eleven (11) pages).

Luecking et al., "3D-Printed Individual Labware in Biosciences by Rapid Prototyping: A Proof of Principle," Engineering in Life Sciences, Jan. 1, 2015, vol. 15, No. 1, pp. 51-56 (Six (6) pages).

D.R. Maule, "A Century of Fermenter Design," J. Inst. Brew., Centenary Review, Mar.-Apr. 1986, vol. 92, pp. 137-145 (Nine (9) pages).

International Preliminary Report on Patentability (PCT/IB/326 & PCT/IB/373) issued in PCT Application No. PCT/US2017/038670 dated Dec. 25, 2018, including English translation of document C2 (Japanese-language Written Opinion (PCT/ISA/237) previously filed on Dec. 3, 2018) (13 pages).

\* cited by examiner

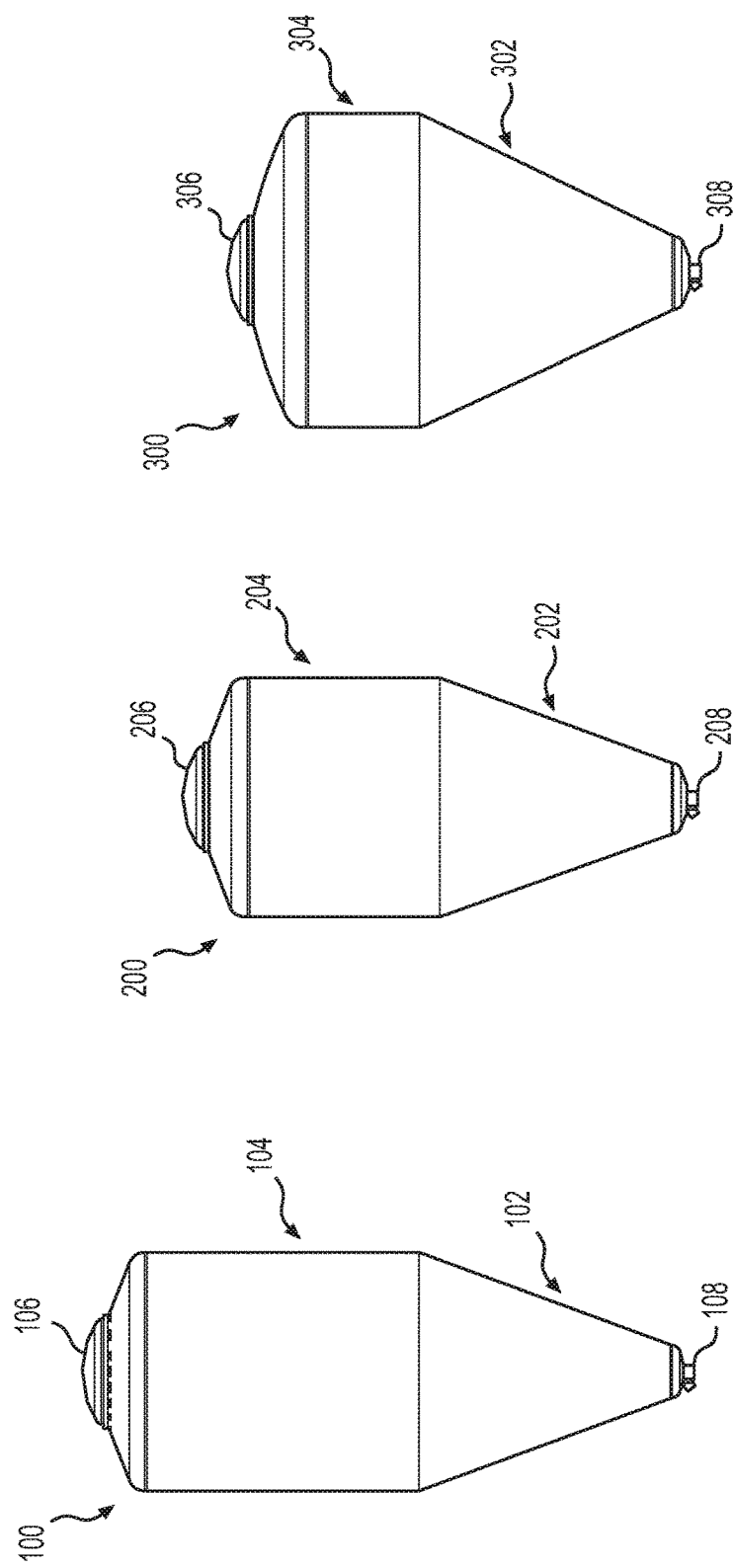

VARIABLE DIAMETER BIOREACTORS

CROSS REFERENCE TO RELATED APPLICATIONS

This application claims priority to and the benefit of U.S. Provisional Application No. 62/354,216, filed Jun. 24, 2016, the contents of which are incorporated herein by reference.

FIELD OF THE INVENTION

The present disclosure relates to bioreactors, and more specifically, to production of biologic material.

BACKGROUND

Typically, production of biologic material is accomplished through the use of bioreactor trains. These trains consist of multiple bioreactors that scale from small inoculation reactors up to full production volumes. These typical bioreactors are dimensioned such that liquid height is greater than vessel diameter; that is, typical bioreactors have a height to width aspect ratio that is greater than 1:1 however, at low volumes (1/20 of the working volume) typical reactors have a very low aspect ratio (liquid height to vessel width). These low aspect ratios are known to cause difficulties in sparging, mixing, and ultimately can lead to difficulties in cell growth and unwanted cell death. Typical bioreactors are designed and sized to scale up the volume of the culture from inoculum in progressively increasing volume seed reactors until sufficient culture volume for production of the desired product has been reached in the production bioreactor. Typically bioreactors are designed to be of fixed diameter and with dished heads and bottoms. The bioreactors are typically constructed with stainless steel tanks, but can also have a disposable liner, a disposable bag and the like.

As such, production scale bioreactor processing suffers from large bioreactor train footprints, high cleaning costs, unwanted lag time and lost seed time when switching between reactors in the train. Each seed bioreactor involves a transfer from one bioreactor to another and introduces the culture to conditions that differ from the end of the previous bioreactor. This typically produces a "lag phase" effect where the cell growth stalls for a period before attaining exponential growth again. For large scale, this typical processing requires multiple reactors resulting in increased facility footprint, and increased preparation activities resulting in increased production time and costs. For example, a 20,000 liter (L) desired production volume bioreactor train can consist of a 200 L inoculation bioreactor (designated N−3), followed by a 1000 L seed bioreactor (designated N−2), followed by a 5000 L seed bioreactor (designated N−1) and finally a 20,000 L volume bioreactor (designated N). This multi-reactor train leads to more clean-in-place (CIP) cycles and associated CIP systems, more steam-in-place (SIP), bioreactor start-up steps, increased draw on utilities (water, steam, waste), complicated plant scheduling and operational execution activities, and greater risk of contamination.

Therefore, improved production scale bioreactor processing devices, systems, and methods are desired.

SUMMARY OF THE INVENTION

The present invention provides a variable diameter bioreactor vessel configured for production of biologic material.

The present invention also provides a variable diameter bioreactor vessel configured for mammalian cell production.

A variable diameter bioreactor vessel is described that can include a first vessel section having a first diameter configured to hold a liquid media and biologic material and a second vessel section having a second diameter that is greater than the first diameter such that the liquid media can be increased from a first volume to a second volume within the vessel. In some aspects, the first vessel section can have an aspect ratio of greater than 0.3:1. In some aspects, the second vessel section can have an aspect ratio of greater than 0.3:1. In some aspects, the liquid media comprises an inoculant. The first vessel section can be configured to be an initial inoculation stage bioreactor. The second vessel section can be configured to be a growth stage or seed bioreactor. The variable diameter bioreactor vessel can further include at least one agitator. In some aspects the bioreactor can further include at least one of an agitator shaft, an agitator, such as an impeller, a sparger, a probe port, a fill port, a condenser, a vent filter, a foam breaker plate, a sample port, a level probe, and a load cell. In some aspects, the variable diameter bioreactor vessel can be configured for growing mammalian, insect, plant, avian or microbial cells.

In other aspects, a variable diameter bioreactor system includes a bioreactor vessel having a first diameter and a second diameter such that the diameter of the vessel varies along a height of the vessel, an agitator disposed within the bioreactor vessel such that the agitator provides desired agitation at a given liquid height of the bioreactor vessel, and a control system operable to scale up the bioreactor vessel from a first volume to a second volume. In some aspects, the first vessel section has an aspect ratio of greater than 0.3:1 and the second vessel section has an aspect ratio of greater than 0.3:1. The first section of the vessel can be an initial inoculation stage bioreactor. The second section of the vessel can be a growth stage vessel section. The variable diameter bioreactor system can also include a sparger, a probe port, a fill port, a condenser, a vent filter, a foam breaker plate, a sample port, a level probe, and/or a load cell. In some aspects, the variable diameter bioreactor system is configured for mammalian cell production.

In other aspects, a method of producing a fermentation product includes inoculating a bioreactor at a first volume with a growth media and inoculum and adding additional growth media to the bioreactor to scale up the bioreactor volume to a second volume following completion of an inoculation stage. In some aspects, the method can further include adding additional growth media to the bioreactor to scale up the bioreactor volume to a third volume following completion of a growth stage. In some aspects, the inoculum is a mammalian cell. In other aspects, the bioreactor can have a minimum aspect ratio of 0.3:1.

In one aspect of the disclosure, the variable diameter bioreactor vessel configured for mammalian cell production includes a vessel configured to hold a liquid media and biologic material; the vessel has a design such that the base of said vessel section is narrower than the top of said vessel; and the vessel is such that the liquid media and biologic material can be increased from a first volume to a second volume within the vessel.

In another aspect of the disclosure, the variable diameter bioreactor vessel configured for mammalian cell production includes a first vessel section having a first diameter configured to hold a liquid media and biologic material; the first vessel section having a conical design such that the base of said first vessel section is narrower than the top of said first vessel section, a second vessel section where the diameter of the bottom of said second vessel section is the same as that of the top of said second vessel section; and the second vessel section is situated such that the liquid media and biologic material can be increased from a first volume to a second volume within the vessel.

In another aspect of the disclosure, a variable diameter bioreactor system is provided which includes a bioreactor vessel having a first diameter and a second diameter such that the diameter of the vessel varies along a height of the vessel; at least one agitator disposed within the bioreactor vessel such that the agitator provides desired agitation at a given liquid height of the bioreactor vessel; and a control system operable to scale up the bioreactor vessel from a first volume to a second volume.

In another aspect of the disclosure, a method of producing a fermentation product using a reduced amount of reactors in a seed stage train and production reactor is provided which includes the steps of inoculating a variable diameter bioreactor at a first volume with a growth media and inoculum; adding additional growth media to the variable diameter bioreactor to scale up the variable diameter bioreactor volume from the first volume to a second volume following completion of an inoculation stage in the first volume; adding additional growth media to the variable diameter bioreactor to scale up the variable diameter bioreactor volume from the second volume to a third volume following completion of a seed stage in the second volume.

In another aspect of the disclosure, a bioproduction facility is provided which includes an initial inoculum growth reactor, a variable diameter bioreactor in fluid communication with the inoculum growth reactor such that the variable diameter bioreactor is configured to be a seed stage reactor train.

The variable diameter bioreactors of the present invention can be built such that they can be used at any scale, beginning with the small volumes of the inoculation stage, up through and including the production scale of 20,000 L. However, variable diameter bioreactors of the present invention can also be used as part of a bioreactor train, such as that described in U.S. Pat. No. 9,670,446, the entirety of which is incorporated by reference.

BRIEF DESCRIPTION OF THE DRAWINGS

The description herein will be more fully understood in view of the following drawings:

FIG. 1 is a side view of a variable diameter bioreactor (VDB);

FIG. 2 is a side view of a variable diameter bioreactor (VDB);

FIG. 3 is a side view of a variable diameter bioreactor (VDB);

DETAILED DESCRIPTION

Figure 4:
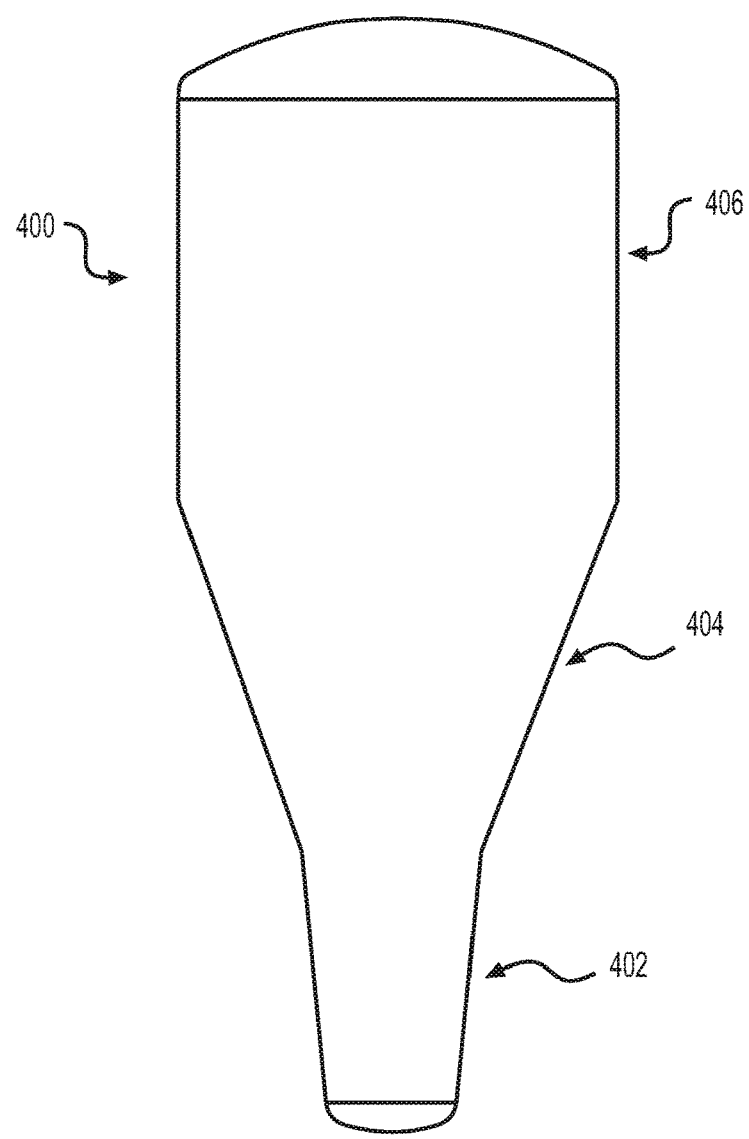
FIG. 4 is a schematic view of a variable diameter bioreactor (VDB)

As stated above, the present disclosure relates to systems, devices, and methods of culturing cellular biologic material in a bioreactor vessel, which are now described in detail with accompanying figures. It is noted that like reference numerals refer to like elements across different embodiments.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

Bioreactor processing of biologic material—including but not limited to microbial and mammalian cultures—in Variable Diameter Bioreactors (VDB), such as those described herein, is designed to sustain growth conditions starting with a minimal inoculum, utilize a continuous and/or bolus, medium and/or feed addition over the growth duration to sustain cell growth, and obtain a sufficient volume of culture for producing the desired product. By accomplishing cell growth and production in a single VDB, multiple smaller volume bioreactors can be eliminated. A single VDB will reduce the overall footprint of bioreactor equipment needed for production of desired product, eliminate multiple seed reactors, multiple CIP's, SIP's, start-up operations, post run operations and minimizes non-logarithmic cell growth or lag phase effect currently observed with the use of multiple seed bioreactors thus simplifying the overall facility operation resulting in time and cost savings.

For example a single 20,000 L VDB can replace a 200 L N-3, 1000 L N-2 and 5000 L N-1 seed bioreactor. It is also estimated that the replacement of 3 seed bioreactors by a single VDB can save greater than 300 square foot of clean room space.

In some aspects, utilizing a conical or smaller diameter cylindrical geometry for the lower portion of the bioreactor and a cylindrical design for the upper portion allows for controllable scale-up within one bioreactor providing key design benefits in relation to mixing and aeration. For example, using a variable diameter conical or smaller diameter cylindrical bottomed tank, with an aspect ratio of greater than 1:1 (liquid height to vessel width at liquid level) can be maintained to support minimal inoculation volume with sufficient liquid head for oxygen transfer during bulk up to larger volume culture. The culture volume can then be bulked up through addition of media to sustain cell growth. The alternative bottom design can enable a higher aspect ratio and ability to operate at lower volumes compared to typical fixed diameter cylindrical tank bioreactor designs.

As used herein, "biologic material" is understood to mean particles consisting, in all or in part, of cellular or viral material, either living or dead, and/or products produced and expressed by cellular or viral cultures. For example, this can include eukaryotic or prokaryotic cells, such as bacteria, mammalian, plant, fungal, viruses such as talimogene laherparepvec (T-VEC), or any other desired therapeutic or biochemical product. In some aspects, "biologic material" includes cells produced for cellular therapy programs. In some aspects, "biologic material" includes viruses produced for virotherapy including viral gene therapy, viral immunotherapy, or protozoal virotherapy. In some aspects, "biologic material" includes cellular or viral cultures for fermentation production of desired compounds including but not limited to proteins, polypeptides, polymers, DNA, RNA, antigens, monoclonal antibodies, or any other desired compound. In some aspects, the biologic material can include inert material such as a substrate or immobilization material. Moreover, as used herein, "liquid media" is understood to mean any liquid typically used in bioreactor processes such as growth media, water, inoculum, and biologic material. The liquid media can have solid particles and/or gas suspended, emulsified, entrained, or otherwise present in the liquid media.

As is shown in the Figures, variable diameter bioreactors can have multiple configurations that allow for the efficient scale-up from inoculum to seed and production within a single bioreactor vessel or with a reduced number of reactors from conventional inoculum to seed to production trains. In some aspects, variable diameter bioreactors can have more suitable aspect ratios when bioreactor media volume is low relative to traditional vertical cylinder uniform diameter reactors. The addition of media or feed from low volume inoculation up to production volume also provides a stabilized environment for cell growth as waste is diluted and fresh nutrients are continuously introduced and mixed. In some aspects, example variable diameter bioreactors can be configured for fermentation processes and can be batch, fed-batch, or continuous and the method of production can change depending upon the stage of culture and volume stage within the bioreactor vessel. For example, during the initial inoculation stage, a batch or fed-batch process can be used. Then, once the cell-growth stage has reached maturity and the bioreactor volume is scaled up to its desired limit, a fed-batch or continuous or perfusion process could be utilized. The variable diameter bioreactors described herein can be formed of any suitable material and can be configured for single-use, disposable systems, including, but not limited to, those described in U.S. application Ser. No. 15/613,954, filed on Jun. 5, 2017. In some aspects, the reactors can be configured for use in mono-type systems or in multiproduct suites.

Further, Variable Diameter Bioreactors can be configured to have any desired total volume. As will be discussed in more detail, VDB's can have about 20,000 liters (L) total volume but it is also possible to design a VDB with 1,000 L total volume, for example, or even 10 L total volume. For example, a 10 L total volume VDB could also be used for process development or scale down studies whereas a 1000 L volume can serve as a pilot scale bioreactor. FIGS. 1-3 illustrate example variable diameter bioreactors having a conical lower portion and a cylindrical upper portions whereby the height of the upper cylindrical portions are varied to achieve various desired volumes.

FIG. 1 illustrates a variable diameter bioreactor (VDB) 100. The variable diameter bioreactor 100 comprises a first vessel section 102 having a first diameter configured to hold a liquid media or culture of biologic material such as appropriate cells and a second vessel section 104 having a second diameter that is greater than the first diameter such that the liquid media can be increased from a first volume to a second volume within the vessel 100. The variable diameter bioreactor 100 also has at least one inlet, such as a manway 106, and at least one outlet 108.

FIG. 2 illustrates a variable diameter bioreactor (VDB) 200 with a decreased height of an upper cylindrical portion relative to the height of the upper cylindrical portion of the variable diameter bioreactor shown in FIG. 1. The variable diameter bioreactor 200 comprises a first vessel section 202 having a first diameter configured to hold a liquid media and a second vessel section 204 having a second diameter that is greater than the first diameter. The variable diameter bioreactor 200 also has at least one inlet, such as a manway 206, and at least one outlet 208.

FIG. 3 illustrates a variable diameter bioreactor (VDB) 300 with a decreased height of an upper cylindrical portion relative to the height of the upper cylindrical portion of the variable diameter bioreactor shown in FIG. 2. The variable diameter bioreactor 300 comprises a first vessel section 302 having a first diameter configured to hold a liquid media and a second vessel section 304 having a second diameter that is greater than the first diameter. The variable diameter bioreactor 300 also has at least one inlet, such as a manway 306, and at least one outlet 308.

FIG. 4 illustrates a variable diameter bioreactor (VDB) 400. The variable diameter bioreactor 400 comprises a first vessel section 402, a second vessel section 404, and a third vessel section 406. The first vessel section has a diameter that varies along the height of the vessel—that is, the diameter of the first vessel section 402 and the diameter of the second vessel section 404 increases towards the top of the bioreactor 400. As shown, however, the diameter of the third section 406 stays relatively uniform throughout the section 406.

Figure 5:
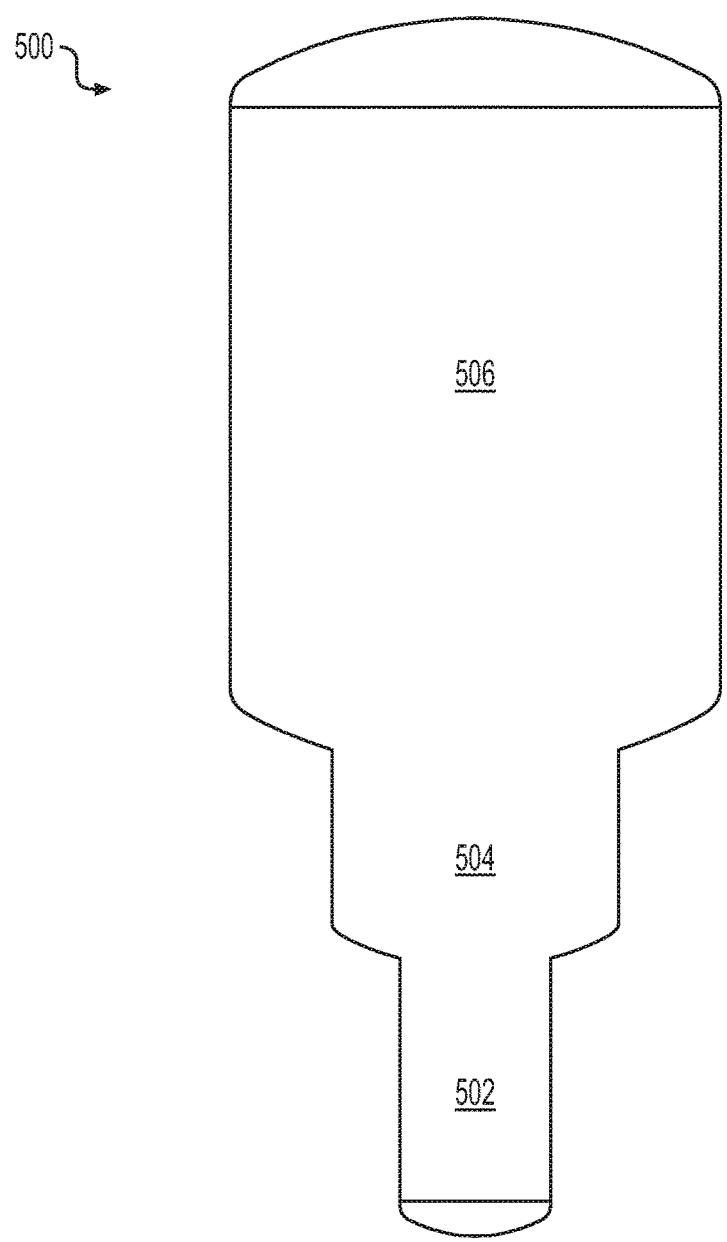
FIG. 5 is a schematic view of a variable diameter bioreactor (VDB)

FIG. 5 illustrates a variable diameter bioreactor (VDB) 500. The variable diameter bioreactor 500 comprises a first vessel section 502, a second vessel section 504, and a third vessel section 506. The vessel has a diameter that varies along the height of the vessel in a step-wise fashion—that is with movement up the vessel the diameter of the third vessel section 506 is greater than the volume of the second vessel section 504, which is greater than the volume of the first vessel section 502. As is shown, in this aspect, the diameter of each stage is uniform throughout the stage with a step increase between the first vessel section 502 and second vessel section 504, and another step increase in diameter between second vessel section 504 and third vessel section 506.

FIGS. 6-9 illustrate example aspect ratios and volumes of various bioreactor designs. As described above, aspect ratio is defined as vessel height to width or diameter. As shown, the reactors of FIGS. 6-9 can have volumes ranging between about 0 liters and 25,000 liters (L).

Figure 6:
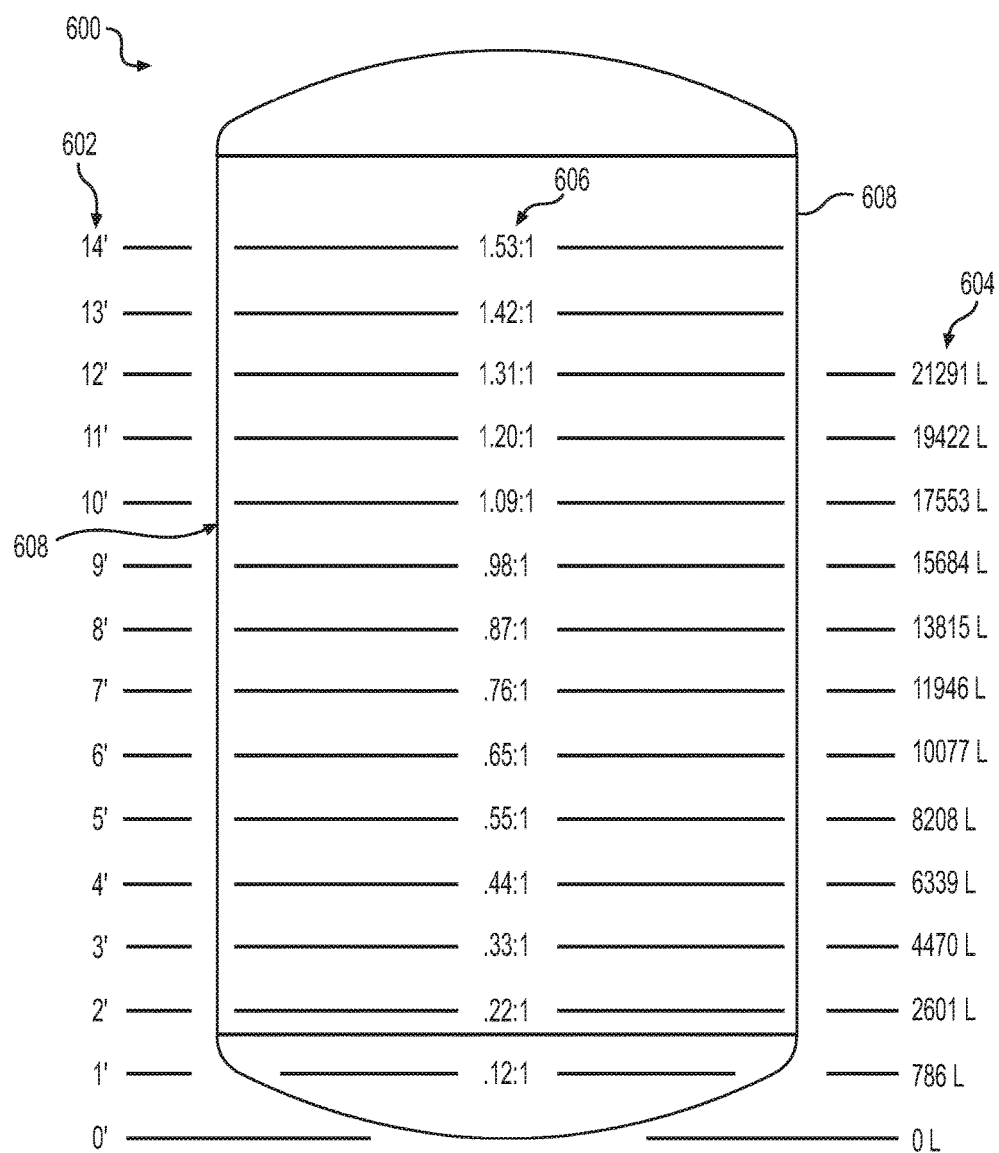
FIG. 6 is a schematic view of a typical bioreactor having a uniform diameter.

FIG. 6 is a typical bioreactor 600 having a uniform diameter (i.e., not a variable diameter bioreactor). The typical bioreactor 600 has only a single vessel section 608 and has a bioreactor height 602, volume 604, and aspect ratio 606. The typical bioreactor 600 has the bioreactor height 602, and aspect ratio 606 shown in Table 1. As shown, at low volumes, e.g. 800 L, the aspect ratio of typical uniform diameter reactors is significantly lower than 0.3. Further, uniform diameter bioreactors need to be operated at an aspect ratio of at least 0.65 or higher, which in FIG. 6 represents a volume of about 10,000 L. Thus a uniform diameter bioreactor requires multiple seed bioreactors of progressively increasing culture volumes so as to achieve the desired culture volume for optimal operation.

TABLE 1

Typical Bioreactor 600

| Height in Feet (602) | Aspect Ratio (606) |
|---|---|
| 0 | 0 |
| 1 | 0.12:1 |
| 2 | 0.22:1 |
| 3 | 0.33:1 |
| 4 | 0.44:1 |
| 5 | 0.55:1 |
| 6 | 0.65:1 |
| 7 | 0.76:1 |
| 8 | 0.87:1 |
| 9 | 0.98:1 |
| 10 | 1.09:1 |
| 11 | 1.20:1 |
| 12 | 1.31:1 |
| 13 | 1.42:1 |
| 14 | 1.53:1 |

Figure 7:
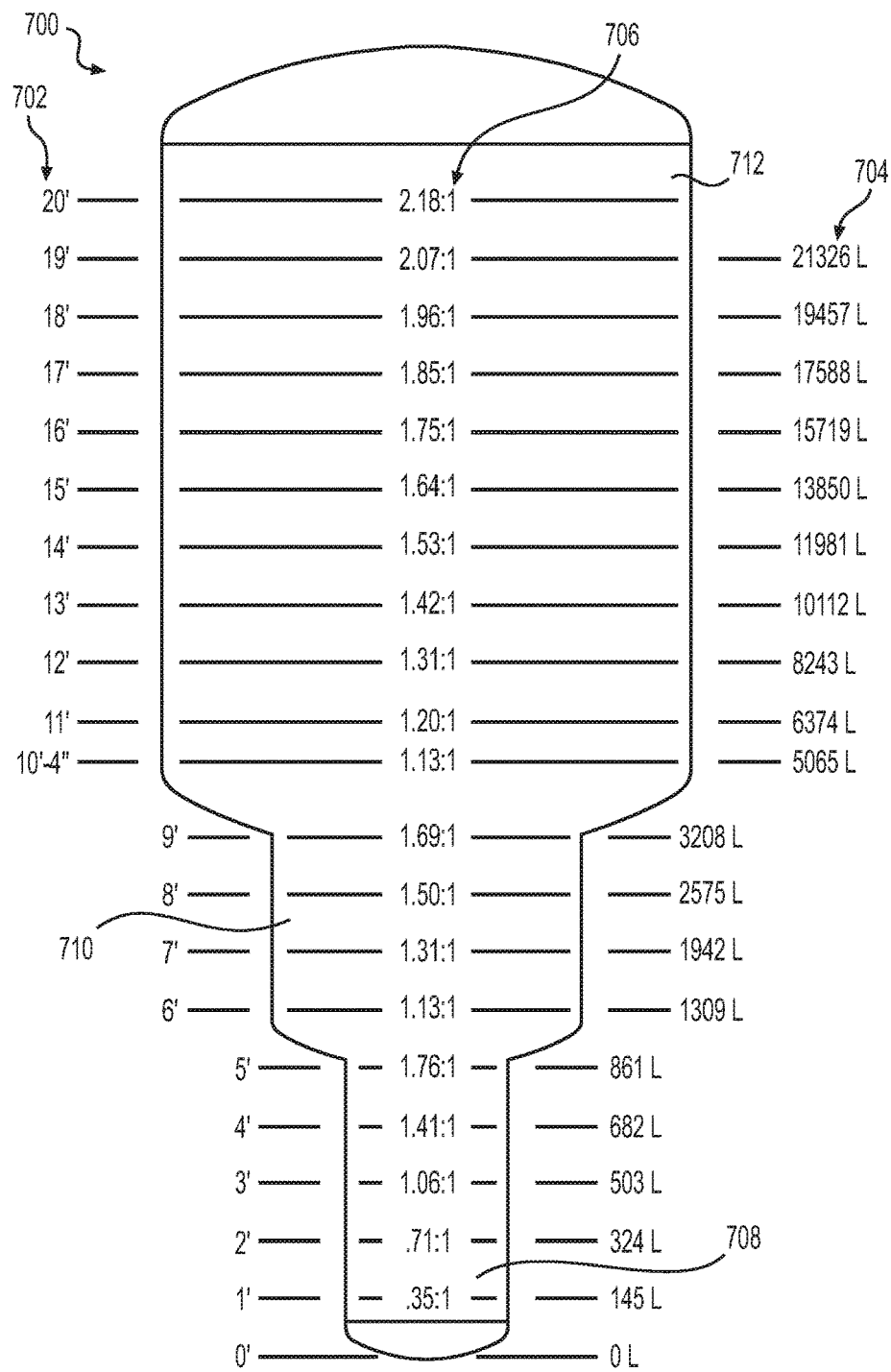
FIG. 7 is a schematic view of an example variable diameter bioreactor (VDB)
Figure 8:
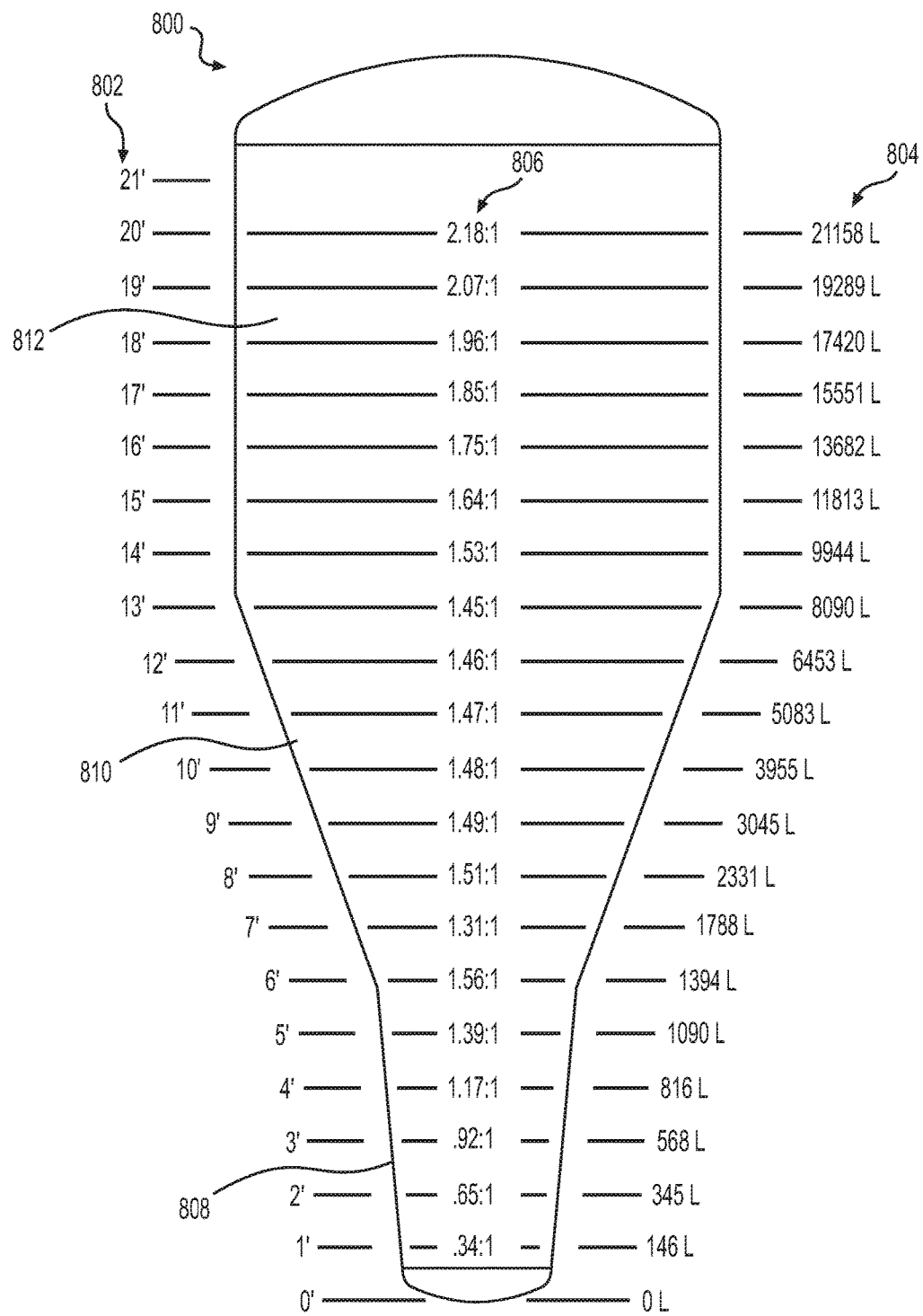
FIG. 8 is a schematic of an example variable diameter bioreactor (VDB)
Figure 9:
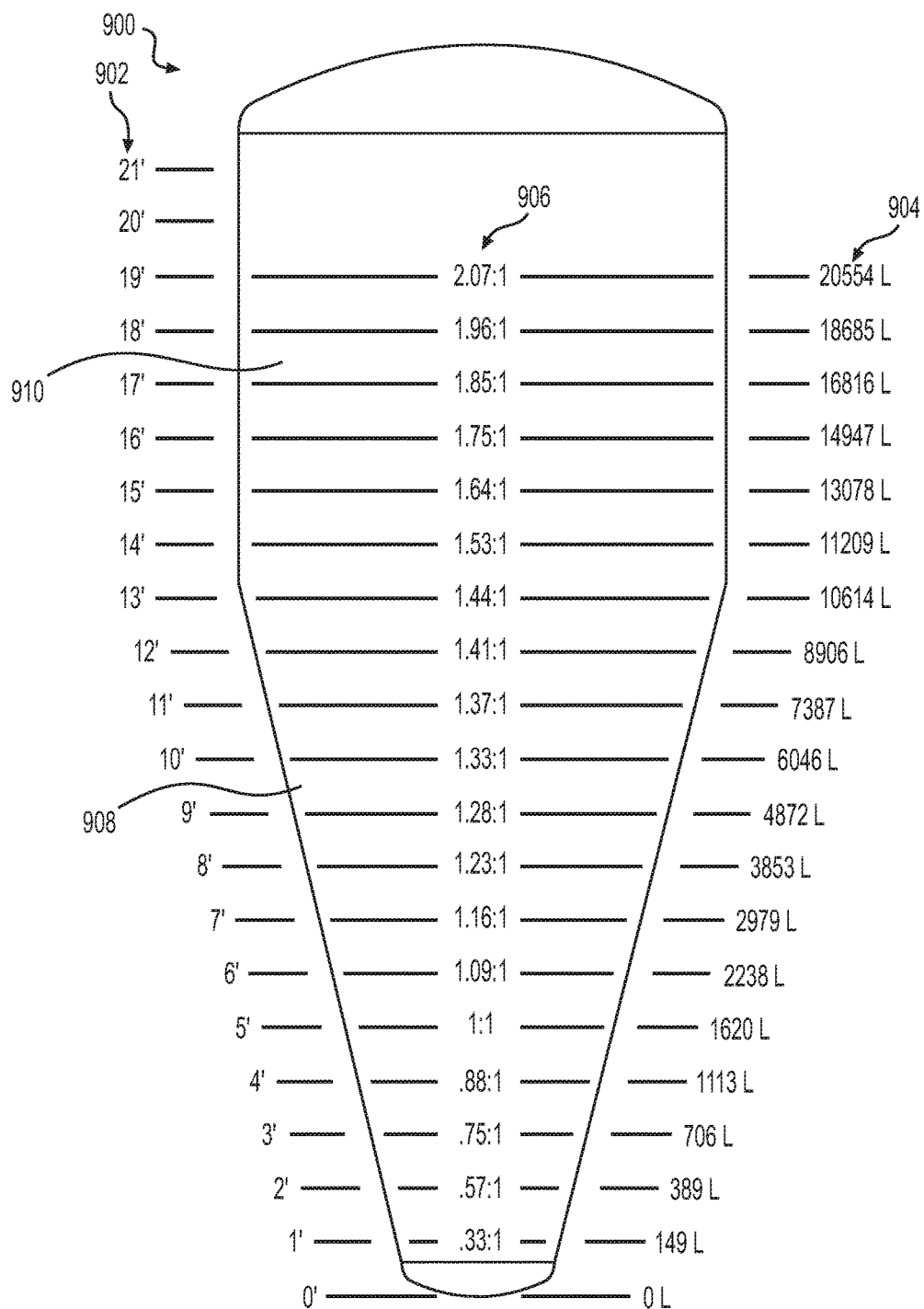
FIG. 9 is a schematic of an example variable diameter bioreactor (VDB)

FIGS. 7, 8 and 9 show variable diameter bioreactors of different configurations all capable of operating at the desired volumes required to eliminate multiple seed bioreactors of 200 L, 1000 L and 4000 L respectively.

FIG. 7 illustrates an example variable diameter bioreactor (VDB) 700 having a bioreactor height 702, volume 704, and aspect ratio 706. As shown, the bioreactor 700 has a first vessel section 708, a second vessel section 710, and a third vessel section 712. Example bioreactor 700 has the bioreactor height 702, aspect ratio 706, and volume 704 shown in Table 2.

TABLE 2

VDB Bioreactor 700

| Height in Feet (702) | Aspect Ratio (706) |
|---|---|
| 0 | 0 |
| 1 | 0.35:1 |
| 2 | 0.71:1 |
| 3 | 1.06:1 |
| 4 | 1.41:1 |
| 5 | 1.76:1 |
| 6 | 1.13:1 |
| 7 | 1.31:1 |
| 8 | 1.50:1 |
| 9 | 1.69:1 |
| 10 | 1.13:1 |
| 11 | 1.20:1 |
| 12 | 1.31:1 |
| 13 | 1.42:1 |
| 14 | 1.53:1 |
| 15 | 1.64:1 |
| 16 | 1.75:1 |

TABLE 2-continued

VDB Bioreactor 700

| Height in Feet (702) | Aspect Ratio (706) |
|---|---|
| 17 | 1.85:1 |
| 18 | 1.96:1 |
| 19 | 2.07:1 |
| 20 | 2.18:1 |

FIG. 8 illustrates an example variable diameter bioreactor (VDB) 800 having a bioreactor height 802, volume 804, and aspect ratio 806. As shown, the bioreactor 800 has a first vessel section 808, a second vessel section 810, and a third vessel section 812.

FIG. 9 illustrates an example variable diameter bioreactor (VDB) 900 having a bioreactor height 902, volume 904, and aspect ratio 906. As shown, the bioreactor 900 has a first vessel section 908, and a second vessel section 910. Example reactors 800, 900 have the bioreactor height 802, 902 and aspect ratio 806, 906 shown in Table 3.

TABLE 3

VDB Bioreactor 800 & 900

| Height in Feet (802, 902) | Bioreactor 800 Aspect Ratio (806) | Bioreactor 900 Aspect Ratio (906) |
|---|---|---|
| 0 | | |
| 1 | 0.34:1 | 0.33:1 |
| 2 | 0.65:1 | 0.57:1 |
| 3 | 0.92:1 | 0.75:1 |
| 4 | 1.17:1 | 0.88:1 |
| 5 | 1.39:1 | 1:1 |
| 6 | 1.56:1 | 1.09:1 |
| 7 | 1.31:1 | 1.16:1 |
| 8 | 1.51:1 | 1.23:1 |
| 9 | 1.49:1 | 1.28:1 |
| 10 | 1.48:1 | 1.33:1 |
| 11 | 1.47:1 | 1.37:1 |
| 12 | 1.46:1 | 1.41:1 |
| 13 | 1.45:1 | 1.44:1 |
| 14 | 1.53:1 | 1.53:1 |
| 15 | 1.64:1 | 1.64:1 |
| 16 | 1.75:1 | 1.75:1 |
| 17 | 1.85:1 | 1.85:1 |
| 18 | 1.96:1 | 1.96:1 |
| 19 | 2.07:1 | 2.07:1 |

Figure 10:
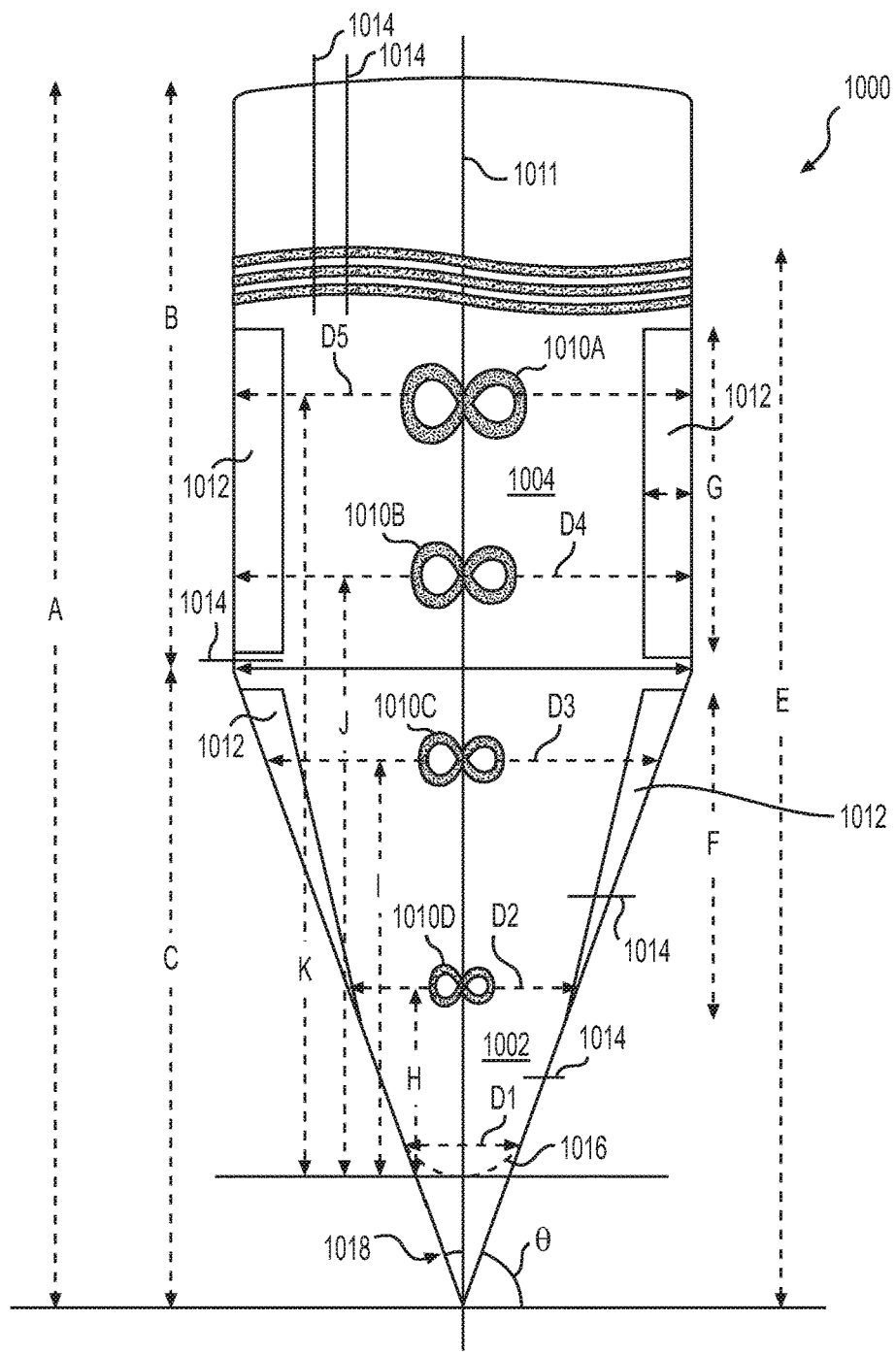
FIG. 10 is a schematic of an example variable diameter bioreactor (VDB)
Figure 11:
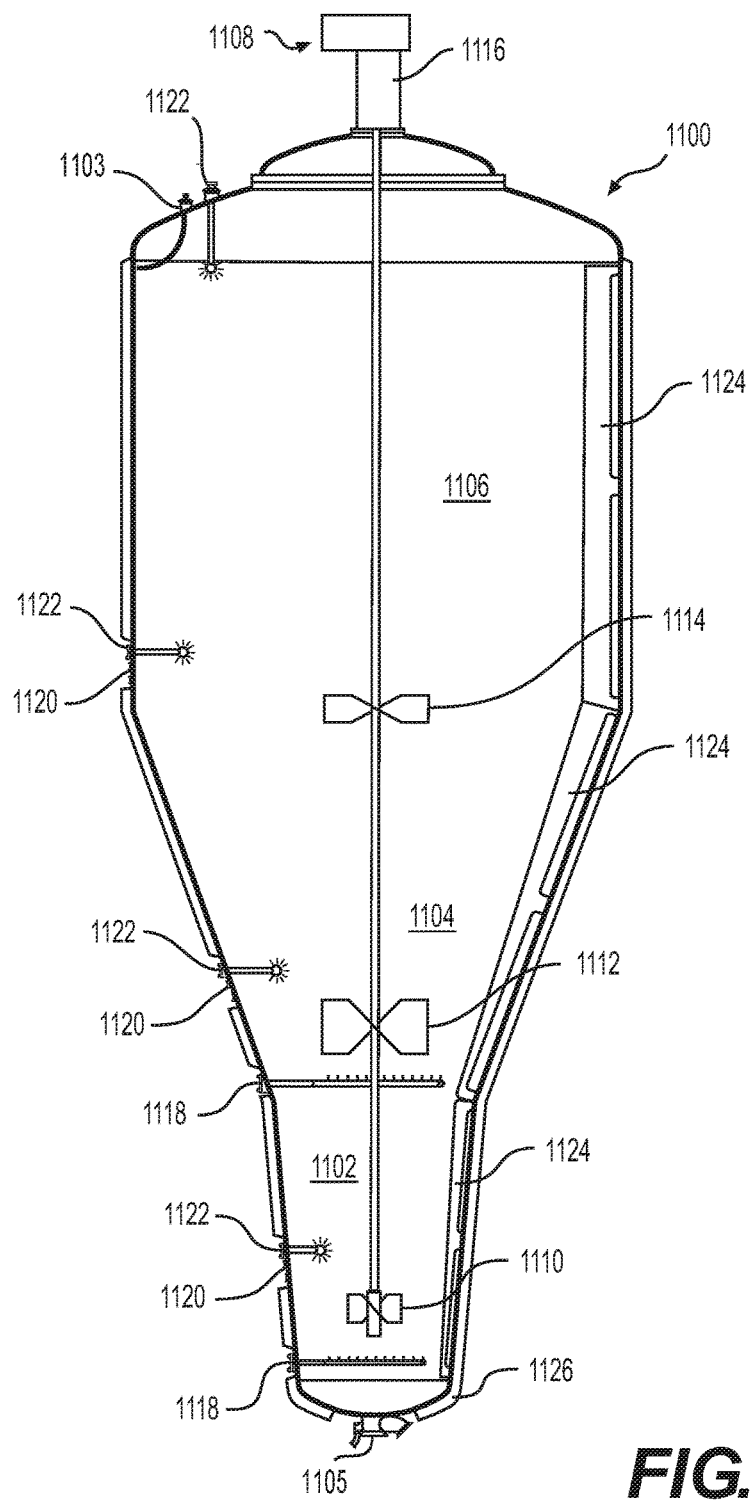
FIG. 11 is a schematic of an example variable diameter bioreactor (VDB) bioreactor.

FIGS. 10 and 11 illustrate example variable diameter bioreactor vessel 1000 and 1100. As is shown, the variable diameter bioreactors 1000, 1100 can have a variety of ports, probes, spargers and other components such as at least one of an agitator shaft, an agitator, such as an impeller, a sparger, a probe port, a fill port, a condenser, a vent filter, a foam breaker plate, a sample port, a level probe, and a load cell.

FIG. 10 is a schematic of VDB 1000 having a first vessel section 1002 and a second vessel section 1004. In some aspects, the first vessel section 1002 has a diameter that increases such that the first vessel section 1002 is a cone shape. The second vessel section 1004 can have a constant diameter such that it has a cylindrical shape. As shown, the VDB 1000 can have a total bioreactor height A. In some aspects, the total bioreactor height A can be in the range of about 5 feet to about 50 feet. For example, total bioreactor height can be about 20 feet. Additionally, as shown, an upper portion of the bioreactor can have a height B, the lower portion can have a height C, and the bioreactor can have a liquid height E. The liquid height E can vary based upon what stage of production is desired. In some aspects, the diameter of the lower portion can vary along height C and in some aspects the diameter of the upper portion can remain constant along height B.

As described herein, the diameter of the VDB bioreactor can vary as with movement along the total bioreactor height A or lower portion height C. As shown, the first vessel section 1002 can have a diameter that increases as a function of the lower portion height C. Movement up the reactor height A increases the diameter, for example to a second diameter D2, third diameter D3, and fourth diameter D4. In some non-limiting aspects, for example, D1 can be about 1 feet to about 3 feet, D2 can be about 1 feet to about 5 feet, D3 can be about 2 feet to about 10 feet, and D4 can be about 3 feet to about 20 feet. By way of one non-limiting example, the VDB bioreactor height A can be about 20 feet with a lower portion height C (cone height) of about 15 ft, an upper portion diameter (D4) of about 10 ft, a bottom diameter (D1) of about 2 ft, a D2 of about 3.25 feet, and a D3 of about 4.8 feet, yielding about a 24,909 liter (L) total volume, 13,789 L lower portion (cone) volume, and 11,120 L upper portion (cylinder) volume. Note that in some aspects, such as is shown in FIG. 10, the upper portion can have a uniform diameter such that D4 is equal to D5. Moreover, as shown the lower portion can have a cone shape having an angle θ that can be any angle suitable to provide the desired diameters and volumes for the lower portion. It is appreciated that the volume capacity can have a dished bottom 1016 and it is appreciated that the angled vertex 1018 is shown merely for explanatory purposes and need not be present in the reactor.

Moreover, the VDB 1000 includes a plurality of agitators 1010*a*, 1010*b*, 1010*c*, and 1010*d*. The agitators can be configured to provide agitation configured for the particular vessel section 1002, 1004 that the particular agitators 1010*a*, 1010*b*, 1010*c*, and 1010*d* is disposed in. As shown, agitator 1010*d* can be disposed within the bioreactor at a height H, agitator 1010*c* can be disposed within the bioreactor at a height I, agitator 1010*b* can be disposed within the bioreactor at a height J, and agitator 1010*a* can be at a height K. For example heights H, I, J, K can be in the range of about 1 foot to about 20 feet. In some aspects, the agitators can have a single drive (not shown) that is disposed along the midpoint 1011 of the VDB 1000. In some aspects, the VDB 1000 can include baffles 1012 throughout the bioreactor 1000. As shown, the baffles 1012 can extend along a height G or F of the bioreactor. In some aspects, the VDB 1000 can include a plurality of ports 1014. The ports 1014 can be configured to be inlets, outlets, probes such as pH, temperature, oxygen, or any other desired probe or sensor. VDB 1000 can also include a single agitator, such as a single impeller.

FIG. 11 is a schematic of an example VDB bioreactor 1100. The VDB bioreactor 1100 has an inlet port 1103 and a bottom outlet valve 1105 configured to add and remove bioreactor media. The VDB bioreactor 1100 can have a first vessel section 1102, a second vessel section 1104, and a third vessel section 1106. The bioreactor has an agitator 1108 that includes a lower agitator 1110, a middle agitator 1112, an upper agitator 1114, and an agitator motor and drive 1116. Moreover, the bioreactor can include at least one sparger 1118 configured to allow for air or other nutrients to be bubbled through the bioreactor liquid media. Additionally, the bioreactor can include at least one probe or addition port 1120. The bioreactor can also include at least one CIP port 1122. As shown, the bioreactor can be configured to have a sparger 1118, probe and addition port 1120, and CIP port 1122 in each of the vessel sections 1102, 1104, 1106. The bioreactor can include any suitable control system for controlling the bioreactor systems including monitoring and controlling sparging, liquid media addition and removal, cell growth and production, oxygen levels, volumes, temperature, pH, and any other desired component. In some aspects, the control system is configured to scale up the bioreactor volume in either a continuous or batch-wise manner. Additionally, the bioreactor can have at least one baffle 1124 disposed therein that is configured to provide suitable mixing conditions without causing undue stress on the bioreactor inoculum, which can lead to apoptosis. Additionally, the bioreactor can include a heat transfer shell 1126 which can have external insulation. VDB 1100 can also include a single agitator, such as a single impeller.

The variable diameter bioreactors described herein can have any cross-sectional shape. In some aspects, the variable diameter bioreactors can have cross-sectional shapes that are non-circular. In the case of non-circular cross-sections, "diameter" is understood to mean the cross-sectional area of each stage. That is, in some aspects, the variable diameter bioreactor can have a cross-sectional shape that is any geometric shape including but not limited to circular, square, rectangular, triangular, pentagonal, hexagonal, octagonal, heptagonal, decagonal, and any other.

The variable diameter bioreactors of the present invention can also include agitators. For instance, the agitator can comprise (i) orbital shaking or rocking to create surface ripples, which permits mixing of the surface layer with the liquid bulk; (ii) an acentrically positioned agitator on an agitator shaft or an agitator mounted off-center on conical shaped vessel bottom which permits axial mixing by vortexing of fluid around the agitator zone; (iii) centrally mounted agitator(s) in an unbaffled vessel with a complex base/base plate design to permit axial deflection of radial flowing liquid bulk; and (iv) non-circular vessel (cube) stirred vessels to overcome the lack of axial flow due to lack of baffles.

In one embodiment, an agitator comprising at least one blade element is used as an aerator. The blade element can be foldable towards the rotatable shaft. In one embodiment, the rotatable shaft is coupled to a first agitator and a second agitator and both agitators can include at least one blade element that is foldable. There can also be a retaining ring position and an agitator disengaging position for holding the agitator in an upright position during mixing or in a collapsed and folded position respectively.

In one embodiment, the rotatable shaft comprises a metallic reinforcing rod surrounded by a shaft sleeve. The metallic reinforcing rod, which can be made from stainless steel, can be made from multiple pieces that are attached together. The top of the reinforcing rod can include a magnetic member for magnetically engaging a motor. The shaft sleeve can be comprised of a polymeric material. The agitator on the shaft can also be made from a polymeric material, such as a hydrophilic polymer. For example, the shaft sleeve and the agitator can comprise a polyethylene polymer that has been modified by being subjected to irradiation, photo or plasma induction, or oxidation. With regard to acentrically positioned agitators, a single agitator mounted off-center offers some advantage in allowing a contiguous change in operating volume during a fed-batch process without having to consider the impact of the liquid surface being cut by the un-submerged rotating agitator.

In accordance with the present disclosure, a rotatable shaft can be coupled to a top impeller and to a bottom impeller. Both the top impeller and the bottom impeller can be made from a polymer material. For instance, in one embodiment, the impellers may be 3-D printed. The top impeller and the bottom impeller can both define a hydrophilic surface. For instance, the polymer material used to form the impellers can comprise a hydrophilic polymer or can comprise a polymer that has been surface modified so as to render the surface hydrophilic.

In one embodiment, for instance, the top and bottom impeller are made from a polyolefin polymer, such as polyethylene or polypropylene. In one embodiment, low density polyethylene can be used. The low density polyethylene can be modified by being subjected to irradiation, photo or plasma induction, or oxidation to form a hydrophilic surface.

In another embodiment, the variable diameter bioreactor of the present invention can be designed such that it maintains the proportions and characteristics as discussed in U.S. Pat. No. 9,670,466, the entirety of which is incorporated by reference. For example, the variable diameter bioreactor of the present invention can have two impellers. The top impeller can comprise a hydrofoil impeller. The bottom impeller, on the other hand, can comprise a four pitched-bladed high solidity impeller. The impeller to tank diameter ratio can be from about 0.35 to about 0.55, such as from about 0.44 to about 0.46. The top impeller and the bottom impeller can have power numbers ($N_p$) of from about 0.1 to about 0.9 and can have flow numbers ($N_q$) of from about 0.4 to about 0.9.

Non-limiting examples of impellers suitable for use in the agitation system of the present disclosure include hydrofoil impellers, high-solidity pitch-blade impellers, high-solidity hydrofoil impellers, Rushton impellers, pitched-blade impellers, gentle marine-blade impellers, CelliGen cell-lift impeller, A320 Impeller, HE3 Impeller, and the like. Spin filters can also be used, such as when the device is operating in perfusion mode. In multi-impeller embodiments of the single-use bioreactor of the present disclosure, the impellers may comprise the same or different materials, designs, and methods of manufacture. For example, in one embodiment, the top impeller could be a hydrofoil impeller or one of like design, such as that made using a 3D printer.

Figure 12:
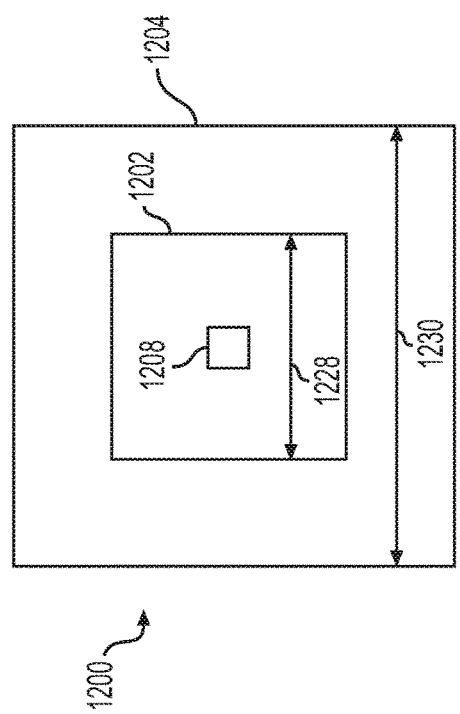
FIG. 12 is a top down view of an example variable diameter bioreactor (VDB)

FIG. 12 is a top-down view of an example bioreactor vessel 1200 having a variable cross-section that is non-circular. That is, the bioreactor 1200 has a cross-sectional shape that is square. In particular, vessel 1200 has a bottom 1208, a first vessel section 1202 having a first diameter 1228 configured to hold a liquid media and biologic material, and a second vessel section 1204 having a second diameter 1230 that is greater than the first diameter 1228 such that the liquid media and biologic material can be increased from a first volume to a second volume within the vessel 1200 that is configured to hold a liquid media and biologic material. A person of ordinary skill in the art would understand that such shape configuration, when viewed from the side could come in any or all of the embodiments depicted in FIGS. 1-11, as well as others disclosed herein. For example, the increase in volume size could be achieved by varying the diameter on one of the four sides, two of the four sides, three of the four sides, or all four sides. These increases need not be contiguous on any or all sides.

In one embodiment, impellers suitable for use herein include those manufactured by 3-D printing to look like any of the impellers known in the art, even if the scale of the impellers is different.

Figure 13:
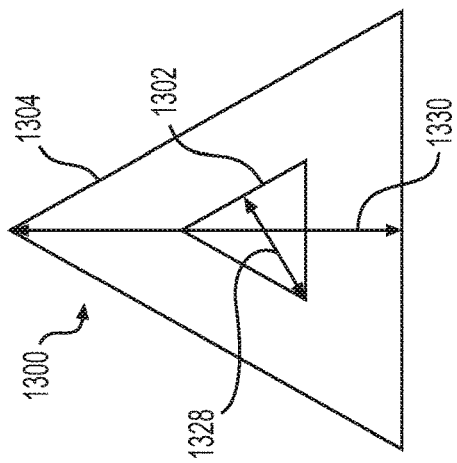
FIG. 13 is a top down view of an example variable diameter bioreactor (VDB).

FIG. 13 is a top-down view of an example bioreactor vessel 1300 having a variable cross-section that is non-circular. That is, the bioreactor vessel 1300 has a cross-sectional shape that is triangular. In particular, vessel 1300 has a first vessel section 1302 having a first diameter 1328 configured to hold a liquid media and biologic material, and a second vessel section 1304 having a second diameter 1330 that is greater than the first diameter 1328 such that the liquid media and biologic material can be increased from a first volume to a second volume within the vessel 1300 that is configured to hold a liquid media and biologic material. A person of ordinary skill in the art would understand that such shape configuration, when viewed from the side could come in any or all of the embodiments depicted in FIGS. 1-11, as well as others disclosed herein. For example, the increase in volume size could be achieved by varying the diameter on one of the three sides, two of the three sides, or all three sides. These increases need not be contiguous on any or all sides.

It will be understood by a person of ordinary skill in the art that other non-circular bioreactors are disclosed herein, such as elliptical, hexagonal, octagonal, etc.

With regard to a non-circular vessel geometry, such as a cubic geometry in FIG. 12 and triangular geometry in FIG. 13, the radial flow produced by an agitator can deflect upon impacting each of the four sides of the vessel. Such designs offer advantages for installation into a steel shell as each corner of the flat-packed bioprocess container can be easily aligned with the corners of the steel shell during installation.

In use, the variable diameter bioreactors described herein can be used to culture live cells and produce biologic material allowing for the efficient use of floor space by limiting the necessary reactors within a train to a single bioreactor. Specifically, the production of biologic material—such as producing a fermentation product—can be achieved in a single VDB bioreactor by inoculating a bioreactor at a first volume with a growth media and inoculum and adding additional growth media to the bioreactor to scale up the bioreactor volume to a second volume following completion of an inoculation stage. In some aspects, use of the bioreactor can include adding additional growth media to the bioreactor to scale up the bioreactor volume to a third volume following completion of a growth stage.

That is, by condensing an inoculation bioreactor and all necessary follow-on growth or seed reactors into a single bioreactor vessel, the footprint of a particular plant is minimized. For example, for a 20,000 liter (L) desired production volume a single 20,000 L bioreactor can be used that consists of a first vessel section (i.e., inoculation vessel section), a second seed or growth section, and a third seed or growth vessel section. For example, the first vessel section (inoculation vessel section) can have a first diameter corresponding to about 100 L to about 200 L volume and a desired aspect ratio of between about 0.3:1 to about 2:1. Next, the second and third seed vessel sections can scale up the bioreactor volume to the desired 20,000 L quantity maintaining a range of desired aspect ratios. For example, the aspect ratios can remain between about 0.3:1 and about 3:1. The 20,000 L bioreactor unit can perform one or more, or all, of the following: feeding of nutrients and/or carbon sources, injection of suitable gas (e.g., oxygen), flow of fermentation or cell culture medium, separation of gas and liquid phases, maintenance of growth temperature, maintenance of pH level, agitation (e.g., stirring), and/or cleaning/sterilizing.

For example, this 20,000 L example bioreactor can be, in some aspects, inoculated at a first volume with a growth media and inoculum, such as a mammalian cell. In this inoculation stage, the reactor can be inoculated at a first volume such that the volume of the reactor is suitable for initial growth of the inoculum. Following a suitable period of time to allow the desired cell growth, the bioreactor can be scaled up to a second reactor volume to achieve a second growth stage of the inoculum. That is, additional growth media and any other desired component required for growth can be added to the bioreactor to scale up the bioreactor volume to a second volume following completion of the inoculation stage. This second volume can be any desired volume that is suitable for the desired continuing growth conditions needed for the inoculum. At this second volume further cell growth and proliferation can be achieved. In some aspects, a third, fourth, or any number of increasing volume growth stages can be utilized to continue the scaling up of the reactor volume to a desired volume.

The variable diameter bioreactors as described herein can be used in many types of manufacturing facilities, including but not limited to, those disclosed in U.S. patent application Ser. No. 15/455,836, filed on Mar. 10, 2017 and Publication No. WO/2017/072201 A2, the entireties of both of which are incorporated by reference. In such facilities, the variable diameter bioreactors of the present invention can replace one or more of the bioreactors discussed in those applications or other like facilities.

The variable diameter bioreactors of the present invention can also be regulated by control system known to a person of ordinary skill in the art, including, but not limited to, those disclosed in U.S. application Ser. No. 15/613,954, filed on Jun. 5, 2017, U.S. patent application Ser. No. 15/612,769 filed on Jun. 2, 2017, U.S. Provisional Patent Application No. 62/451,470 filed on Jan. 27, 2017, and others.

Examples

The relationship between the volume, diameter and properties for cell growth of the variable diameter bioreactors of the present invention requires the consideration of many factors. The below equation provides a useful guide when designing bioreactors of the present invention:

$$\text{Sphere: } V = \frac{\pi}{3} y^2 (1.5D - y)$$

$$\text{Cylinder: } V = \frac{LD^2}{8}(\theta - \sin(\theta)) \quad T = 2\sqrt{y(D-y)} = D\sin\left(\frac{\theta}{2}\right)$$

$$\text{Cone: } V = \frac{\pi h}{12}(D_{bot}^2 + D_{bot}D_{top} + D_{top}^2) \quad z = \frac{1}{2h}(D_{top} - D_{bot})$$

For example, when designing the bioreactor of the present invention to work with volumes up to 20,000 L, the variable diameter bioreactor would have the following proportions:
Total Volume: 20,000 L
Cone Volume: 15,000 L
Diameter$_{top}$: 7 ft
Diameter$_{bottom}$: 3 ft
Total Height: 30.2 ft
Cylinder Volume: 5,000 L
Cone Height: 25.6 ft
Cylinder Height: 4.6 ft As another example, when designing the bioreactor of the present invention to fit into a certain space in a manufacturing facility or the like, where the height is limited to twenty feet, the above equation would yield the following proportions:
Total Volume: 16,458 L
Cone Volume: 9,341 L
Diameter$_{top}$: 8 ft
Diameter$_{bottom}$: 2 ft
Total Height: 20 ft
Cylinder Volume: 7,117 L
Cone Height: 15 ft
Cylinder Height: 5 ft The above example can have four impellers, such as that depicted in FIG. 10.

As another example, the design of the present invention allows variable diameter bioreactors to be built in excess of 20,000 L, which is new to the art. Specifically, a variable diameter bioreactor could be built with the following proportions:
Total Volume: 25,000 L
Cone Volume: 15.000 L
Diameter$_{top}$: 7.9 ft
Diameter$_{bottom}$: 2.5 ft
Total Height: 30 ft
Cylinder Volume: 10,000 L
Cone Height: 22.8 ft
Cylinder Height: 7.2 ft Unless described otherwise above, the above description may be further understood as follows. The devices, facilities and methods described herein are suitable for use in and with culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesized by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2012/0077429; and 2009/0305626; and U.S. Pat. Nos. 9,388,373, 8,771,635, 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EB13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri*, and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. oryzae, A. nidulans*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. oryzae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West $12^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen und Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleukin, denileukin diftitox, interferon alpha-n3 (injection), interferon alpha-n1, DL-8234, interferon, Suntory (gamma-la), interferon gamma, thymosin alpha 1, tasonermin, DigiFab, ViperaTAb, EchiTAb, Cro-Fab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, imiglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enfuvirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestim, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDS-VAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alkaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CIVIL vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table A of US2016/0097074:

TABLE A

| Protein Product | Reference Listed Drug |
|---|---|
| interferon gamma-1b | Actimmune ® |
| alteplase; tissue plasminogen activator | Activase ®/ Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |

TABLE A-continued

| Protein Product | Reference Listed Drug |
|---|---|
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/ Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/ Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone Antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ® |
| interferon alfa-2[a] | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table B.

TABLE B

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/Coagulation Factors | Factor VIIa | NovoSeven |
| | Factor VIII | Bioclate, Helixate, Kogenate, Recombinate, ReFacto |
| | Factor IX | |
| | Antithrombin III (AT-III) | Benefix |
| | Protein C concentrate | Thrombate III Ceprotin |

TABLE B-continued

Exemplary Products

| Therapeutic Product type | Product | Trade Name |
|---|---|---|
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table C.

TABLE C

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech Fresenius Biotech) | BsIgG: Triomab | CD3, HER2 | Retargeting of T cells to tumor | Phase I/II | Advanced solid tumors |

TABLE C-continued

Bispecific Formats

| Name (other names, sponsoring organizations) | BsAb format | Targets | Proposed mechanisms of action | Development stages | Diseases (or healthy volunteers) |
|---|---|---|---|---|---|
| Blinatumomab (Blincyto ®, AMG 103, MT 103, MEDI 538, Amgen) | BiTE | CD3, CD19 | Retargeting of T cells to tumor | Approved in USA<br>Phase II and III<br>Phase II<br>Phase I | Precursor B-cell ALL<br>ALL<br>DLBCL<br>NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tubingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |

TABLE C-continued

Bispecific Formats

| Name (other names, sponsoring organizations) | BsAb format | Targets | Proposed mechanisms of action | Development stages | Diseases (or healthy volunteers) |
|---|---|---|---|---|---|
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGFA | Blockade of 2 proangiogenics | Phase I | Solid tumors |
| RG7716 (Roche) | CrossMab | Ang2, VEGFA | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A variable diameter bioreactor vessel configured for culturing of live cells or cellular biologic material, comprising:
   (a) a vessel configured to hold a liquid medium and the cells or biologic material; and
   (b) an agitator, wherein said vessel has a design such that the base of said vessel is narrower than the top of said vessel,
   wherein said vessel is such that the liquid medium and the cells or biologic material can be increased from a first volume to a second volume within the vessel, and
   wherein the agitator is made using a 3-D printer.

2. A variable diameter bioreactor vessel configured for mammalian cell production, comprising:
   a vessel configured to hold a liquid medium and biologic material,
   wherein said vessel has a design such that the base of said vessel is narrower than the top of said vessel,
   wherein said vessel is such that the liquid medium and biologic material can be increased from a first volume to a second volume within the vessel, and
   wherein the first vessel has a cross-sectional shape that is non-circular.

3. A variable diameter bioreactor vessel configured for mammalian cell production, comprising:
   a vessel configured to hold a liquid medium and biologic material,
   wherein said vessel has a design such that the base of said vessel is narrower than the top of said vessel,
   wherein said vessel is such that the liquid medium and biologic material can be increased from a first volume to a second volume within the vessel, and
   wherein the first vessel has a cross-sectional shape that is square.

4. A variable diameter bioreactor system, comprising:
   (a) a bioreactor vessel having a first diameter and a second diameter such that the diameter of the vessel varies along a height of the vessel, at least from the height of the first diameter to the height of the second diameter;
   (b) at least one agitator disposed within the bioreactor vessel such that the agitator provides desired agitation at a given liquid height of the bioreactor vessel;
   (c) a control system operable to scale up the bioreactor vessel from a first volume to a second volume,
   (d) a sparger,
   (e) a probe port,
   (f) a fill port,
   (g) a condenser,
   (h) a vent filter,
   (i) a foam breaker plate,
   (j) a sample port,
   (k) a level probe, and
   (l) a load cell.

5. The variable diameter bioreactor system of claim 4, wherein the bioreactor vessel is configured to be a production stage bioreactor.

6. The variable diameter bioreactor system of claim 4, wherein there are two agitators.

7. The variable diameter bioreactor system of claim 6, wherein one agitator is a hydrofoil impeller.

8. The variable diameter bioreactor system of claim 4, wherein the bioreactor vessel has an aspect ratio of greater than 0.3:1.

9. The variable diameter bioreactor system of claim 4, wherein the first diameter of the vessel is an initial inoculation stage vessel section.

10. The variable diameter bioreactor system of claim 4, wherein the second diameter of the vessel is a growth stage vessel section.

11. The variable diameter bioreactor system of claim 4, wherein the variable diameter bioreactor vessel is configured for mammalian cell production.

12. The variable diameter bioreactor system of claim 4, wherein the control system is configured to scale up the bioreactor vessel in a batchwise manner.

13. The variable diameter bioreactor system of claim 4, further comprising a disposable bag configured to be disposed within the bioreactor vessel such that the variable diameter bioreactor system is a single use bioreactor system.

14. The variable diameter bioreactor system of claim 4, wherein the system is configured for microcarrier cultures.

15. The variable diameter bioreactor system of claim 4, wherein the system is configured for adherent cultures.

* * * * *